US009849249B2

(12) United States Patent
Bilton et al.

(10) Patent No.: US 9,849,249 B2
(45) Date of Patent: Dec. 26, 2017

(54) DOSE SETTING MECHANISM AND METHOD OF SETTING A DOSE

(75) Inventors: Simon Lewis Bilton, Warwickshire (GB); David Martin Leak, Lake Hopatcong, NJ (US)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 377 days.

(21) Appl. No.: 13/878,761

(22) PCT Filed: Oct. 11, 2011

(86) PCT No.: PCT/EP2011/067675
§ 371 (c)(1),
(2), (4) Date: Apr. 11, 2013

(87) PCT Pub. No.: WO2012/049138
PCT Pub. Date: Apr. 19, 2012

(65) Prior Publication Data
US 2013/0211341 A1    Aug. 15, 2013

Related U.S. Application Data

(60) Provisional application No. 61/392,739, filed on Oct. 13, 2010.

(30) Foreign Application Priority Data

May 31, 2011   (EP) ..................... 11168187

(51) Int. Cl.
*A61M 5/315*   (2006.01)
*A61M 5/31*    (2006.01)

(52) U.S. Cl.
CPC .... *A61M 5/31536* (2013.01); *A61M 5/31535* (2013.01); *A61M 5/31551* (2013.01); *A61M 5/31585* (2013.01); *A61M 2005/3126* (2013.01)

(58) Field of Classification Search
CPC .......... A61M 5/31551; A61M 5/31541; A61M 5/31525; A61M 5/31583; A61M 5/3155;
(Continued)

(56) References Cited

U.S. PATENT DOCUMENTS 533,575 A      2/1895  Wilkens
4,865,591 A *  9/1989  Sams ........................... 604/186
(Continued)

FOREIGN PATENT DOCUMENTS

EP    0937471    8/1999
EP    0937476    8/1999
(Continued)

OTHER PUBLICATIONS

Form PCT/IB/326, Notification Concerning Transmittal of International Preliminary Report on Patentability.

*Primary Examiner* — Nathan R Price
*Assistant Examiner* — Weng Lee
(74) *Attorney, Agent, or Firm* — McDonnell Boehnen Hulbert & Berghoff LLP

(57) ABSTRACT

A dose setting mechanism for a drug delivery device. The mechanism may comprise a drug delivery device housing. A dose dial component is positioned in the housing and rotatable during dose setting and dose delivery. A split threaded insert is in threaded engagement with the dose dial component. The insert can transform from a first configuration to a second configuration when the dose dial component is rotated. In one dose setting mechanism arrangement, the first configuration may comprise a first open configuration and the second configuration may comprise a second closed configuration.

16 Claims, 10 Drawing Sheets

(58) Field of Classification Search
  CPC .......... A61M 5/31501; A61M 5/31533; A61M
    5/31505; A61M 5/31528; A61M
    2005/3126; A61M 5/31535; A61M
    5/31536; A61M 5/31585
  USPC .......................................... 604/186, 207–211
  See application file for complete search history.

(56) References Cited

U.S. PATENT DOCUMENTS

| | | | |
|---|---|---|---|
| 5,226,895 A | 7/1993 | Harris | |
| 5,279,586 A | 1/1994 | Balkwill | |
| 5,304,152 A * | 4/1994 | Sams | A61M 5/31553 604/207 |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 * | 5/2005 | Veasey et al. | 604/208 |
| 2006/0153693 A1 | 7/2006 | Fiechter et al. | |
| 2006/0206057 A1 * | 9/2006 | DeRuntz | A61M 5/31551 604/224 |
| 2009/0264828 A1 * | 10/2009 | Dette et al. | 604/189 |
| 2009/0275914 A1 * | 11/2009 | Harms et al. | 604/506 |
| 2009/0275916 A1 | 11/2009 | Harms et al. | |

FOREIGN PATENT DOCUMENTS

| | | |
|---|---|---|
| WO | 99/38554 | 8/1999 |
| WO | 01/10484 | 2/2001 |
| WO | 2004030730 A2 | 4/2004 |
| WO | 2004078239 A1 | 9/2004 |

* cited by examiner

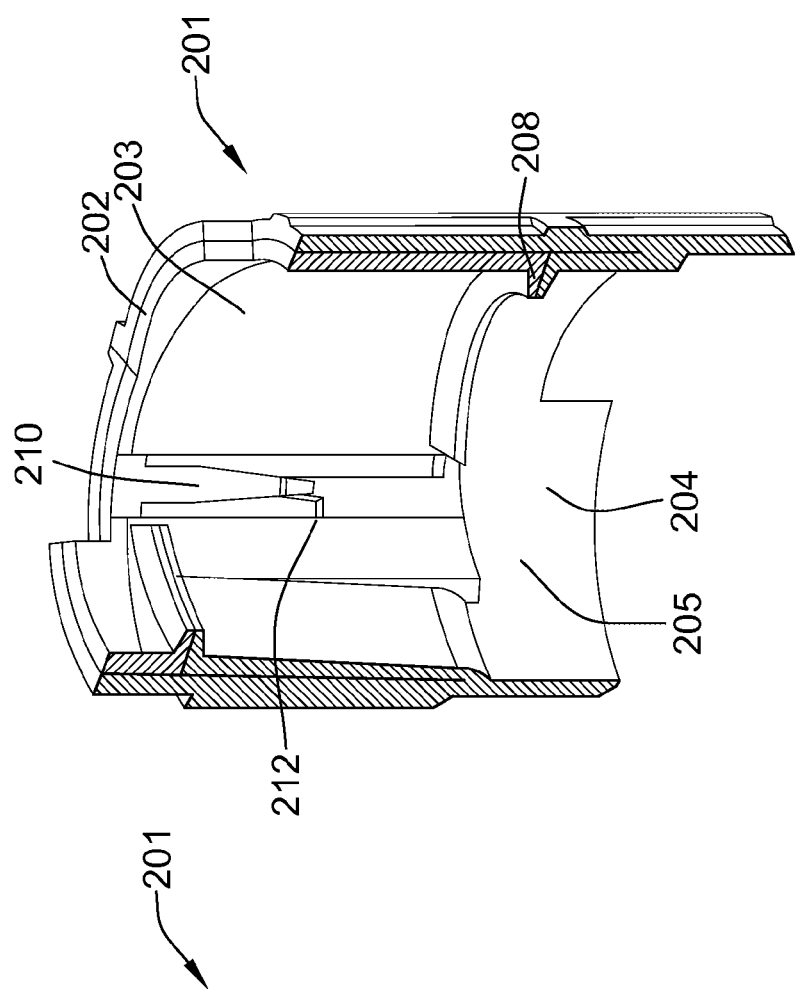
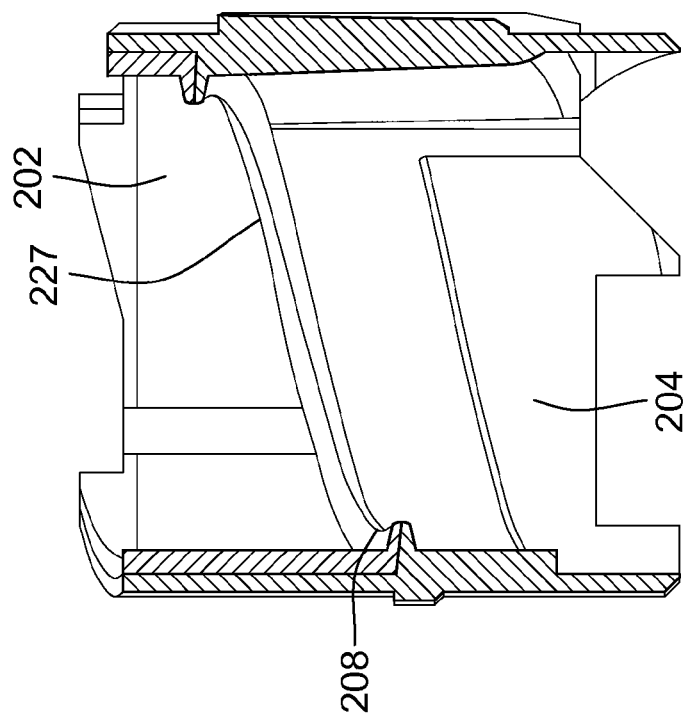
FIG. 6
FIG. 5

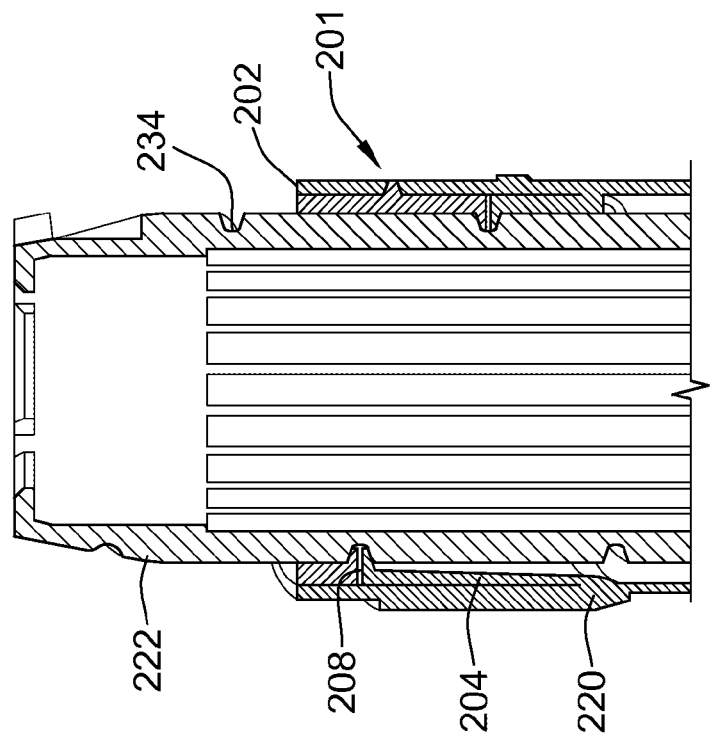
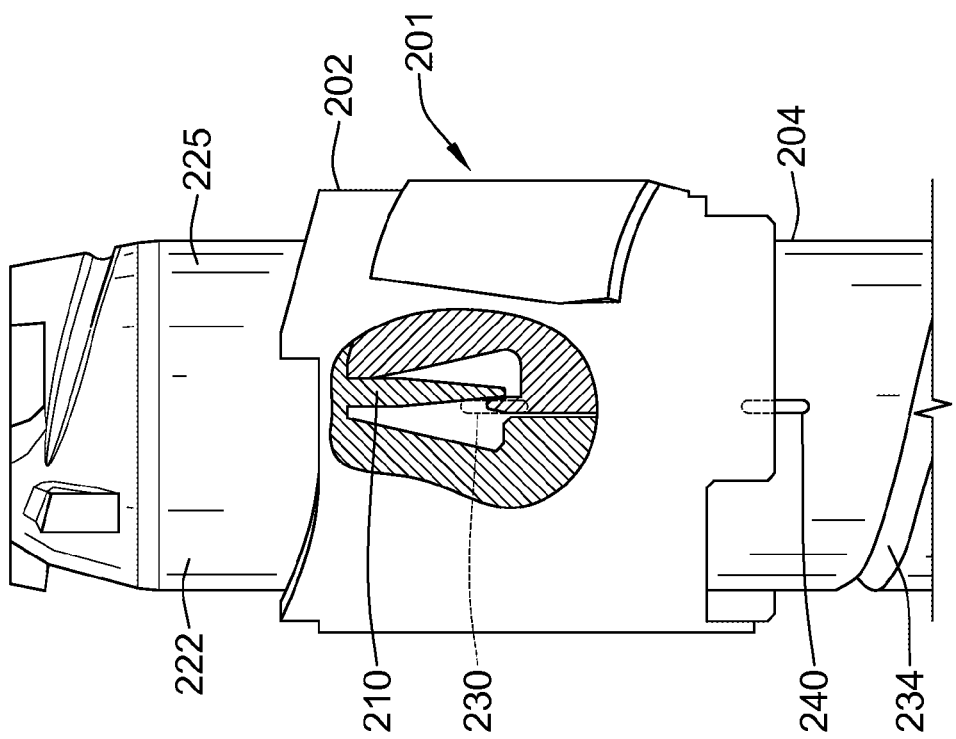

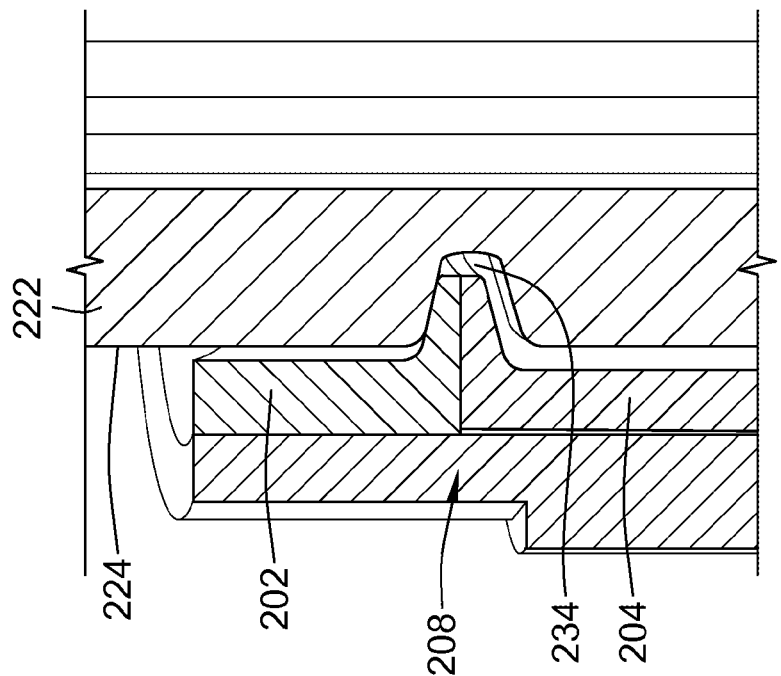
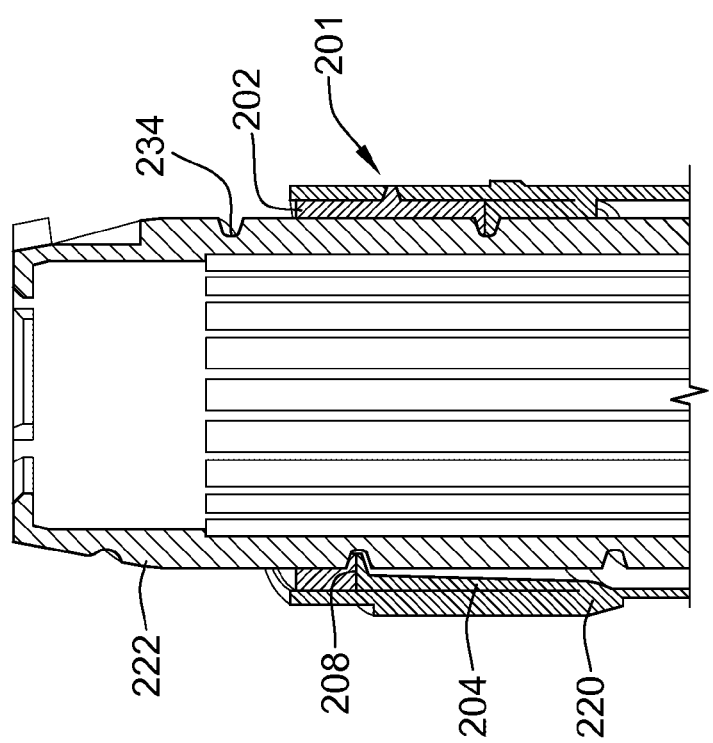

Table 1

| Dialed Insulin Dose | Pen Number | | | |
|---|---|---|---|---|
| | 1 | 2 | 3 | 4 |
| 2 | Low | Low | Low | Low |
| 4 | Low | Low | Low | Low |
| 6 | Low | Low | Low | Low |
| 8 | Low | Low | Low | Low |
| 10 | Dial | Low | Low | Low |
| 12 | Dial | Low | Low | Low |
| 14 | Dial | Low | Low | Low |
| 16 | Dial | Low | Low | Low |
| 18 | Dial | Dial | Low | Low |
| 20 | Dial | Dial | Low | Low |
| 22 | Dial | Dial | Low | Low |
| 24 | | Dial | Low | Low |
| 26 | | Dial | Low | Low |
| 28 | | Dial | Low | Low |
| 30 | | Dial | Low | Low |
| 32 | | Dial | Low | Low |
| 34 | | Dial | Low | Low |
| 36 | | Dial | Dial | Low |
| 38 | | Dial | Dial | Low |
| 40 | | Dial | Dial | Low |
| 42 | | Dial | Dial | Low |
| 44 | | | Dial | Low |
| 46 | | | Dial | Low |
| 48 | | | Dial | Low |
| 50 | | | Dial | Low |
| 52 | | | Dial | Low |
| 54 | | | Dial | Low |
| 56 | | | Dial | Low |
| 58 | | | Dial | Dial |
| 60 | | | Dial | Dial |
| 62 | | | Dial | Dial |
| 64 | | | | Dial |
| 66 | | | | Dial |
| 68 | | | | Dial |
| 70 | | | | Dial |
| 72 | | | | Dial |
| 74 | | | | Dial |
| 76 | | | | Dial |
| 78 | | | | Dial |
| 80 | | | | Dial |

Legend:
- Dose may be dialed and delivered
- Low dose - Cannot be dispensed
- High dose - Cannot be dialed

FIG. 14

Table 2

| Dialed Insulin Dose | Pen 1 | Pen 2 | Pen 3 | Pen 4 |
|---|---|---|---|---|
| 2 | ▨ | ▨ | ▨ | ▨ |
| 4 | ▨ | ▨ | ▨ | ▨ |
| 6 | ▨ | ▨ | ▨ | ▨ |
| 8 | ▨ | ▨ | ▨ | ▨ |
| 10 | ▨ | ▨ | ▨ | ▨ |
| 12 | ▨ | ▨ | ▨ | ▨ |
| 14 | ▨ | ▨ | ▨ | ▨ |
| 16 | ▨ | ▨ | ▨ | ▨ |
| 18 | ▨ | ▨ | ▨ | ▨ |
| 20 | ▨ | ▨ | ▨ | ▨ |
| 22 | ▨ | ▨ | ▨ | ▨ |
| 24 | □ | ▨ | ▨ | ▨ |
| 26 | □ | ▨ | ▨ | ▨ |
| 28 | □ | ▨ | ▨ | ▨ |
| 30 | □ | ▨ | ▨ | ▨ |
| 32 | □ | ▨ | ▨ | ▨ |
| 34 | □ | ▨ | ▨ | ▨ |
| 36 | □ | ▨ | ▨ | ▨ |
| 38 | □ | ▨ | ▨ | ▨ |
| 40 | □ | ▨ | ▨ | ▨ |
| 42 | □ | ▨ | ▨ | ▨ |
| 44 | □ | □ | ▨ | ▨ |
| 46 | □ | □ | ▨ | ▨ |
| 48 | □ | □ | ▨ | ▨ |
| 50 | □ | □ | ▨ | ▨ |
| 52 | □ | □ | ▨ | ▨ |
| 54 | □ | □ | ▨ | ▨ |
| 56 | □ | □ | ▨ | ▨ |
| 58 | □ | □ | ▨ | ▨ |
| 60 | □ | □ | ▨ | ▨ |
| 62 | □ | □ | ▨ | ▨ |
| 64 | □ | □ | □ | ▨ |
| 66 | □ | □ | □ | ▨ |
| 68 | □ | □ | □ | ▨ |
| 70 | □ | □ | □ | ▨ |
| 72 | □ | □ | □ | ▨ |
| 74 | □ | □ | □ | ▨ |
| 76 | □ | □ | □ | ▨ |
| 78 | □ | □ | □ | ▨ |
| 80 | □ | □ | □ | ▨ |

Legend:
- ▨ GLP-1 Dose may be dialed and delivered
- (backslash hatching) Low dose - Cannot be dispensed
- □ High dose - Cannot be dialed

FIG. 15

Table 3

| Dialed long acting Insulin Dose | Premix Pen Number | | | | | |
|---|---|---|---|---|---|---|
| | 1 | 2 | 3 | 4 | 5 | 6 |
| | Mix ratio (insulin :GLP-1) | | | | | |
| | 0.83 | 0.665 | 0.53 | 0.43 | 0.35 | 0.285 |
| 2 | | | | | | |
| 4 | | | | | | |
| 6 | | | | | | |
| 8 | | | | | | |
| 10 | | | | | | |
| 12 | | | | | | |
| 14 | | | | | | |
| 16 | | | | | | |
| 18 | | | | | | |
| 20 | | | | | | |
| 22 | 18.3 | | | | | |
| 24 | 19.9 | | | | | |
| 26 | 21.6 | | | | | |
| 28 | | 18.6 | | | | |
| 30 | | 20.0 | | | | |
| 32 | | 21.3 | | | | |
| 34 | | | 18.0 | | | |
| 36 | | | 19.1 | | | |
| 38 | | | 20.1 | | | |
| 40 | | | 21.2 | | | |
| 42 | | | | 18.1 | | |
| 44 | | | | 18.9 | | |
| 46 | | | | 19.8 | | |
| 48 | | | | 20.6 | | |
| 50 | | | | 21.5 | | |
| 52 | | | | | 18.2 | |
| 54 | | | | | 18.9 | |
| 56 | | | | | 19.6 | |
| 58 | | | | | 20.3 | |
| 60 | | | | | 21.0 | |
| 62 | | | | | 21.7 | |
| 64 | | | | | | 18.2 |
| 66 | | | | | | 18.8 |
| 68 | | | | | | 19.4 |
| 70 | | | | | | 20.0 |
| 72 | | | | | | 20.5 |
| 74 | | | | | | 21.1 |
| 76 | | | | | | 21.7 |
| 78 | | | | | | |
| 80 | | | | | | |

Legend:
- GLP-1 Dose may be dialed and delivered
- Low dose - Cannot be dispensed
- High dose - Cannot be dialed

FIG. 16

DOSE SETTING MECHANISM AND METHOD OF SETTING A DOSE

CROSS REFERENCE TO RELATED APPLICATIONS

The present application is a U.S. National Phase application pursuant to 35 U.S.C. §371 of International Application No. PCT/EP2011/067675 filed Oct. 11, 2011, which claims priority to U.S. Provisional Patent Application No. 61/392,739 filed Oct. 13, 2010 and European Patent Application No. 11168187.0 filed May 31, 2011. The entire disclosure contents of these applications are herewith incorporated by reference into the present application.

FIELD OF INVENTION

The present patent application is generally directed to dose setting mechanisms for drug delivery devices that control minimum and/or maximum possible dose settings and a method of setting and delivering at least a predetermined minimum dose of a medicament. More particularly, the present patent application is generally directed to drug delivery devices, such as pen type drug delivery devices where therapy demands that a patient receive at least a certain minimum dose and not exceed a certain maximum dose of a particular medicament. Such devices provide for self-administration of medicinal product from a multi-dose cartridge and contain dose limiting mechanisms for setting minimum and/or maximum doses. The present application may find application in both disposable and reusable type drug delivery devices. However, aspects of the invention may be equally applicable in other scenarios as well.

BACKGROUND

Self administered injectable medicaments are often delivered using a variable-dose injection device. Prior to the injection the user selects the dose that they require according to their prescribed dose and/or their current or expected future physical condition. A typical example would be an insulin delivery device for diabetics where a patient's dose is determined according to their prescribed dose and their expected food intake and activity level. Typically such devices allow the user to select any dose from 1 unit up to the maximum unit dose that the device can deliver, typically 60 units or 80 units for a manual device, such as a pen-type or syringe injection device.

Pen type drug delivery devices have been designed and developed to perform regular injections by persons without formal medical training. This is increasingly common among patients having diabetes where self-treatment enables such patients to conduct effective management of their disease. Because the patient, and not the health care worker, may be using such a drug delivery device, one requirement is that the device should be robust in construction. The drug delivery device may also be easy to use both in terms of the drug delivery device manipulation and understanding of the device's operation. This is especially true for diabetics who are required to inject themselves repeatedly with insulin solution and the volume of insulin to be injected may vary from patient to patient and even from injection to injection. For at least this reason, certain diabetics may require drug delivery devices that allow the patient to inject successive measured dosages of the same or perhaps different preset volumes of insulin solution accurately and with minimum dexterity challenges. This presents a further design challenge since, in the case of certain diabetics, users may have impaired vision and/or may be physically infirm with limited dexterity.

In addition to insulin, other medicaments require a minimum dose to be delivered before they are therapeutically effective. A variable-dose device that allows the patient to deliver doses below the therapeutically effective minimum dose creates the possibility that the user may deliver the ineffective doses either by an error of dose calculation or by mistakenly selecting the incorrect dose. Likewise, some medicaments require that a maximum dose is not to be exceeded. This may be for safety reasons such as increased risk or severity of side-effects or excessive or unwanted actions of the medicament. Current variable-dose delivery devices typically have a maximum dose that is limited by the maximum dose that the delivery mechanism can provide, however, this does not necessarily relate to the maximum advised or prescribed dose of the medicament.

SUMMARY

It is an object of the invention to provide a device that reduces or eliminates the risk that a user of an injection device will set and administer a dose either below the minimum effective dose or above a safe maximum dose of a particular medicament.

This object is solved with a dose setting mechanism as defined in claim 1. The present invention has at least two applications. First, is the delivery of a single active medicament which must be a variable dose within a defined dose window, i.e. the dose must be more than a certain minimum dose and must not exceed a certain maximum dose. The second application relates to the delivery of a combined formulation of active medicaments where at least one of the medicaments is preferably delivered as a variable dose and at least one other medicament is preferably delivered as a fixed dose, and where this fixed dose can safely be allowed to vary within a defined dose window, for example by ±10% of the nominal fixed dose.

The minimum and/or maximum dose limited delivery device in accordance with our disclosure could be used for a medicament that requires a minimum dose to be delivered before it becomes therapeutically effective, but where a degree of dose adjustment may be required. This dose adjustment may be required for a number of reasons, including tailoring a dose to a patient's body weight or the severity of their medical condition. The minimum and maximum dose limited device (min/max device) may also be used instead of a fully variable (i.e., 0 to max dose) device in order to reduce the possibility for dosing errors by the patient. Using the min/max device rather than a variable dose pen reduces the risk that a patient might accidentally deliver a dose outside the defined dose window, i.e., either too high or too low.

One example of the utility of our min/max device is where a parent could give the min/max delivery device to a child for the child to self-administer and the parent would know that the minimum and maximum levels of the min/max device limited the possible severity of any overdose or under dose. Another example of where such a device might be applicable is for patients who take long acting insulin. Typically a variable dose pen is required when a patient is "titrating" their dose to reach their target blood glucose level. However, once the target blood glucose level has been achieved the dose of long acting insulin typically remains more or less constant over relatively long periods of time. During this period, where their insulin dose is either constant or changes by only a few units on a day-to-day basis, the patient's long acting insulin needs could be effectively met by the minimum and maximum dose limited delivery device.

Table 1 (provided below) shows an example family of delivery devices, "Pen 1" through "Pen 4", which could be used in place of a single 1-80 unit variable dose device. Each of the Pens 1-4 are designed and manufactured around the same basic mechanism, but each pen contains either additional or alternative components which are used to set a different minimum and maximum dose. Patients would be prescribed a particular Pen according to their stable long acting insulin dose. For example, according to Table 1 a patient prescribed 30 units per day of long acting insulin would be prescribed Pen 2, which has a minimum dose of 18 units and a maximum dose of 42 units, respectively. Any number of mechanical components can be used in such a pen design to ensure these predetermined min/max doses, including axial and/or rotational stops, detents, clutches, compressible fingers, or the like components. In an example, a split threaded insert may be configured to a dose dial component to ensure these predetermined min/max doses.

The insulin dose of diabetic patients may change gradually over time. Therefore there may be a small amount of dose range overlap between Pens to allow for a smooth transition between Pens as the dose increases. For example, according to Table 1 a patient prescribed 40 units per day of long acting insulin would be given Pen 2 if they expected their dose to decrease over time or Pen 3 if they expected their dose to increase over time. The number of pens in the "family" and the selected dose ranges shown in Table 1 are illustrative only. By using the min/max device of the present invention a potential mistake when selecting the dose is limited to within the pen's operating window. Dialing a dose above or delivering a dose below the pen's dose range would not be possible and this would alert the patient to their error.

The min/max device may also be applicable for the delivery of other medicines, particularly where there is a risk of confusion with similar devices that may lead to dose errors or drug/device mix-ups. One such example would be rapid acting insulin and long acting insulin. Both of these insulins are measured in "units" however the same number of units of each insulin type will have a very different effect and a patient will be prescribed different doses of each drug to be taken at different times throughout the day. A mix up of long acting and rapid acting insulin can cause hypoglycemia and is potentially fatal. Both types of insulin may be delivered by injection pen devices. Patients perform their injections on such a routine basis that an "automatic pilot" effect can occur where patients have been known to mix up their insulin pens, even though the pens are of different design, color, shape and carry different labels.

The presently proposed min/max device may help to prevent this mix up occurring. For example, assume both rapid acting and long acting insulins were each provided with a family of min/max devices according to Table 1. A patient is prescribed 50 units per day of long acting insulin (which would require long acting Pen 3) and 15 units of rapid acting insulin with meals (which would require Pen 1). The most dangerous mix up could occur if the patient mistakenly delivered 50 units of rapid acting insulin rather than long acting insulin. If the patient attempted to do this with the min/max devices then the patient would pick up the rapid insulin device (Pen 1) and find that they could not dial beyond 22 units. This should alert them to the fact that this is not the correct insulin pen, and therefore the incorrect insulin type, and prevent the incorrect insulin being delivered.

The min/max concepts may be applied equally to both disposable devices and reusable devices.

Certain medicines also require the user to perform a "priming" dose to confirm the correct operation of the delivery device and needle. This is usually accomplished by delivering an "air-shot" of 2 units and then checking that the medicine can be seen coming out of the needle. The min/max concept shown in Table 1 would not permit this. If priming functionality is required a second permissible "dose window", for example ranging from 1-2 units, may also be implemented within each pen mechanism. An example of how this could be applied is shown in Table 2. Although both Tables 1 and 2 show only even numbers of units this is done only for clarity and the device may be configured to deliver odd and even units or potential ½ units.

As mentioned, the presently disclosed devices may also be useful in therapies where the delivery of a combined formulation of active medicaments is needed, where at least one of the medicaments is preferably delivered as a variable dose and at least one other medicament is preferably delivered as a fixed dose. If a patient requires a combination of medicines then there is an advantage if those medicines can be provided as a single formulation (i.e. both drugs are mixed together in predefined proportions and supplied in one primary pack) for delivery by a single injection device in one injection through a single needle. However, if one of the drugs requires the delivery of a user-selectable variable dose and the second drug requires a dose above a minimum dose to be therapeutically effective and must not exceed a given maximum dose, then it is beneficial for the drug delivery device to be configured such that it is prevented from delivering doses that are outside of this range.

For example, a patient may be prescribed a combination therapy of long acting insulin (typically delivered in variable dose devices) and GLP-1 (typically delivered as a fixed dose). GLP-1 is a glucagon-like peptide-1, which is derived from the transcription product of the proglucagon gene and is found in the body where it is secreted by the intestinal L cell as a gut hormone. GLP-1 possesses several physiological properties that make it (and its analogs) a subject of intensive investigation as a potential treatment of diabetes mellitus. In order to avoid the patient having to perform two injections the two medicines are pre-mixed into a single formulation. Since both medicaments are pre-mixed in a fixed ratio it is not possible to vary the long acting insulin dose without also varying the GLP-1 dose. However, it may be acceptable for the GLP-1 dose to vary within a given tolerance, for example ±10%, around a fixed nominal dose. It is therefore possible, using a family of min/max limited devices to provide a family of pre-mix devices which between them will allow delivery of a variable long acting insulin dose and a GLP-1 dose that always falls within ±10% of a given "fixed" dose.

Table 3, for example, shows a family of 6 min/max pen-type injection devices that allow the delivery of any long acting insulin dose from 22-76 units along with a GLP-1 dose that is "fixed" to 20 mg±10%. Each Pen within the family would have different minimum and maximum dose thresholds and would be provided with a primary pack or cartridge of medicament filled with the appropriate mix ratio of the two medicines. The family of pen devices could be provided as disposable mechanical devices, prefilled with the appropriate mix ratio cartridge of medicament. Alternatively, the family of devices could be provided as reusable mechanical devices. In the latter case, the devices would be preferably dedicated to a particular mix ratio cartridge, i.e. only the correct mix ratio cartridge can be loaded into each pen family member.

A third alternative is to provide the "family" of pen devices via a single electronic device that can be programmed with the minimum and maximum dose functionality. Preferably, the min/max electronic device would be loaded with a coded cartridge that would automatically upon being loaded into the device communicate to the device what the required minimum and maximum thresholds should be for that particular cartridge and mix ratio.

One specific means of achieving a minimum settable dose on a variable dose, drug delivery device, such as a pen-type device, is to include a change of state mechanism that prevents dosing of the device until a predetermined minimum dose has been set. A maximum dose mechanism can also be used with a minimum dose mechanism. Examples of pen-type devices that can incorporate the present invention are described in WO 2004/078239 A1. The WO 2004/078239 A1 application describes the structure and functionality of drive mechanisms of the pen-type injection devices, specifically the interaction of a drive sleeve, a clutch means, a dose dial sleeve, a housing and a piston rod during both dose setting and dose delivery. The full description of the pen-type injection devices disclosed in WO 2004/078239 A1 is incorporated herein by reference.

The minimum dose limiting function as disclosed herein may be achieved by means of a split threaded insert. According to one possible exemplary embodiment, a dose setting mechanism for a drug delivery device comprises a drug delivery device housing. A dose dial component is positioned in the housing and rotatable during dose setting and dose delivery for example as disclosed in WO 2004/078239 A1. A split threaded insert is in threaded engagement with the dose dial component. The insert can transform from a first configuration to a second configuration when the dose dial component is rotated. In one dose setting mechanism arrangement, the first configuration may comprise a first open configuration where the split thread form is separated by a gap and the second configuration may comprise a second closed configuration where the split thread form is closed and there is no gap.

In another example, a method of delivering at least a predetermined minimum dose of a medicament is provided. The method includes the steps of providing a dose setting mechanism comprising a housing and rotatably positioning a dose dial component in the housing. The method further includes the step of threadedly engaging a split threaded insert with a portion of the dose dial component and the step of transforming the insert from a first configuration to a second configuration when the dose dial component is rotated.

In another example, a method of setting at least a predetermined allowable minimum dose of a medicament is disclosed. In one arrangement, this method may comprise the steps of inducing a high-friction state in a drug delivery device when a dose less than a predetermined minimum allowable dose is set by the drug delivery device, and inducing a low-friction state in the delivery device when at least a minimum allowable dose is set by the drug delivery device. Whilst in the high-friction state, the user is unable to deliver a dose since the high-friction causes lock-up of the mechanism thread. This is because the injection mechanism relies on the thread back-winding during dose delivery due to the applied axial load, which is very friction sensitive. However, the user is able to manually dial the device to the pre-selected minimum dose since a dialling action does not require thread over-haul due to an axial load. A high-friction state may be defined by e.g. fricition coefficients >0,15 and a low-friction state may be defined by e.g. fricition coefficients <0,15. However, the present invention is not limited to these pure running friction values. Moreover, in the high-friction state the thread is caused to jam even with low fricitional coefficients. In other words, in the high-friction state the thread is not free running, whereas in the low-friction state the thread is free running.

In an example of our min/max device, a user can manually override the minimum dose function if required by dialing a dose equal to, or greater than, the predetermined minimum dose and then dialing back down to the required dose level. Additionally, the dose count numbers (which may be provided on an outer surface of the dose dial component) below the minimum dose may be colored a different color such as red to differentiate that the dose dialed is less than the normal minimum dose.

These as well as other advantages of various aspects of our proposed drug delivery device will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 5 illustrates a close-up sectional view of the split threaded insert illustrated in FIG. 4;

FIG. 6 illustrates another close-up sectional view of the split threaded insert illustrated in FIG. 4;

FIG. 7 illustrates a perspective view of an initial position of the split threaded insert illustrated in FIGS. 4-6 situated along the dose dial component before a dose is selected;

FIG. 8 illustrates a sectional view of the initial position of the split threaded insert and the dose dial component FIG. 7;

FIG. 11 illustrates a sectional view of the second position of the split threaded insert disposed along the dose dial component after the minimal dose has been selected as illustrated in FIG. 10;

FIG. 12 illustrates a close up view of the split threaded insert illustrated in FIGS. 10-11;

FIG. 14 illustrates a table (Table 1) of an example family of delivery devices designated as Pen 1-Pen 4 with minimum and maximum dose thresholds;

FIG. 15 illustrates a table (Table 2) of another example family of delivery devices designated as Pen 1-Pen 4 with minimum and maximum dose thresholds; and FIG. 16 illustrates a table (Table 3) of yet example family of delivery devices designated as Pen 1-Pen 6 with minimum and maximum dose thresholds.

DETAILED DESCRIPTION

Figure 1:
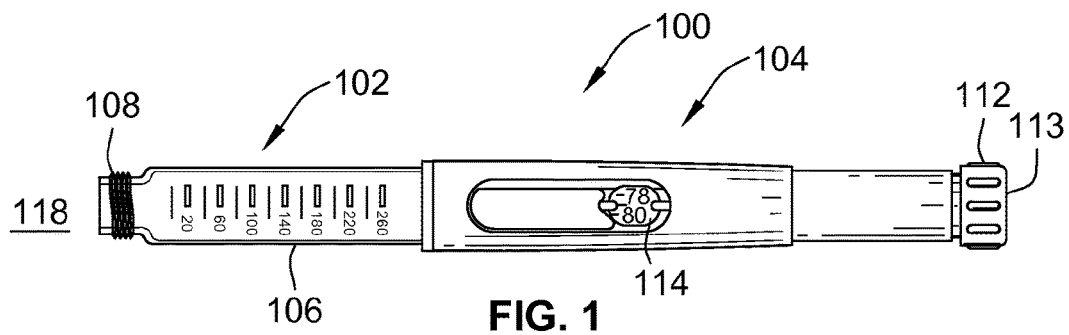
FIG. 1 illustrates an exemplary design of a pen-type drug delivery device.

Referring to FIG. 1, there is shown a drug delivery device 100 in accordance with an exemplary pen-type design arrangement. The drug delivery device 100 comprises a housing having a first cartridge retaining part 102 and a dose setting mechanism 104. The drug delivery device 100 may be a resettable drug delivery device (i.e., a reusable device) or alternatively a non-resettable drug delivery device (i.e., a non-reusable device). A first end of the cartridge retaining part 102 and a second end of the dose setting mechanism 104 are secured together by connecting features. For non-resettable devices, these connecting features would be permanent and non-reversible. For resettable devices, these connecting features would be releasable.

In this illustrated arrangement, the cartridge retaining part is secured within the second end of the dose setting mechanism. A removable cap (not shown) is releasably retained over a second end or distal end of a cartridge retaining part or cartridge housing. The dose setting mechanism 104 comprises a dose dial grip 112 and a window or lens 114. A dose scale arrangement, such as a dose scale arrangement provided along an outer surface of the dose dial sleeve, may be viewable through the window or lens 114. To set a dose of medication contained within the drug delivery device 100, the dose dial grip 112 can be rotated such that a dialed dose will become viewable in the window or lens 114 by way of the dose scale arrangement. As will be described in greater detail below, in one alternative dose setting mechanism arrangement, a visual indication may be provided to a user through a window or lens 114 if less than minimal dose has been dialed. For example, the color red may be seen through the window/lens if a dose less than the minimum dose has been set. In such an exemplary arrangement, once a dose greater than the minimum dose has been set, a numerical dose setting scale may be viewed within the window/lens.

FIG. 1 illustrates the medical delivery device 100 with the cover cap removed from a distal end 118 of the medical delivery device 100. This removal exposes the cartridge housing 106. Preferably, a cartridge (not shown) from which a number of doses of a medicinal product may be dispensed, is provided in the cartridge housing 106. Preferably, the cartridge contains a type of medicament that can be administered relatively often, such as once or more times a day. One such medicament is either long acting or short acting insulin or an insulin analog; however, any medicament or combination of medicaments is possible. The cartridge comprises a bung or stopper that is retained near a second end or a proximal end of the cartridge. The drug delivery device further comprises a drive sleeve and a spindle (not illustrated in FIG. 1, but illustrated as items 224 and 226, respectively, in FIG. 2).

The cartridge housing 106 of the drug delivery device 100 has a distal end and a proximal end. Preferably, the distal end of the cartridge housing 106 comprises a hub 108 for attaching a removable needle assembly. However, other needle assembly connection mechanisms could also be used. If the drug delivery device 100 comprises a resettable device, the cartridge proximal end is removably connected to the dose setting mechanism 104. In one preferred embodiment, cartridge housing proximal end is removably connected to the dose setting mechanism 104 via a bayonet connection. However, as those of ordinary skill in the art will recognize, other types of removable connection methods such as threads, partial threads, ramps and detents, snap locks, snap fits, and luer locks may also be used.

As previously mentioned, the dose setting mechanism 104 of the drug delivery device illustrated in FIG. 1 may be utilized as a reusable drug delivery device. (i.e., a drug delivery device wherein a dose setting mechanism can be reset). Where the drug delivery device 100 comprises a reusable drug delivery device, the cartridge is removable from the cartridge housing 106. With such a reusable drug delivery device, the cartridge may be removed from the device 100 without destroying the device 100 by merely having the user disconnect the dose setting mechanism 104 from the cartridge housing 106.

In use, once the cap is removed, a user can attach a suitable needle assembly to the hub 108 provided at the distal end of the cartridge housing 106. Such needle assembly may be, for example, screwed onto a distal end of the housing 106 or alternatively may be snapped onto this distal end. After use, the replaceable cap may be used to re-cover the cartridge housing 106. Preferably, the outer dimensions of the replaceable cap are similar or identical to the outer dimensions of the dose setting mechanism 104 so as to provide an impression of a unitary whole when the replaceable cap is in position covering the cartridge housing 106 when the device is not in use.

Figure 2:
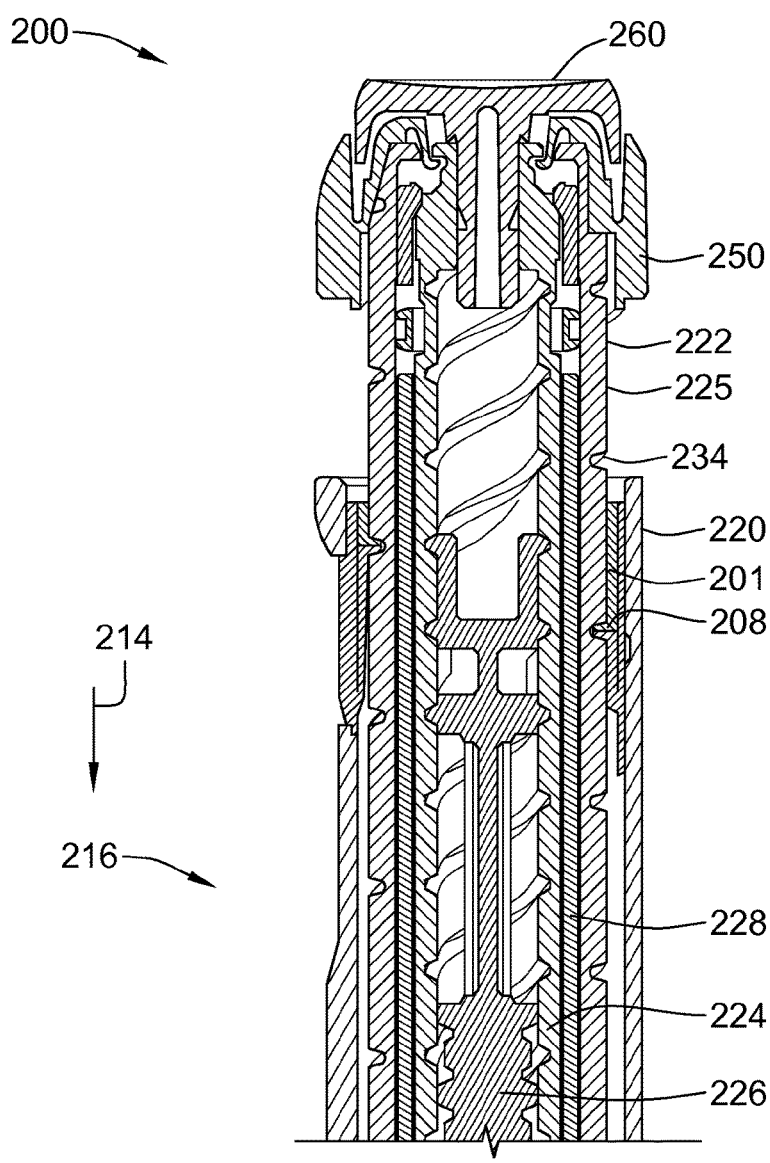
FIG. 2 illustrates a cross-sectional view of a portion of the pen-type drug delivery device illustrated in FIG. 1.

A first exemplary dose setting mechanism in accordance with the present invention is described with reference to FIG. 2. FIG. 2 illustrates a cross-sectional view of a drug delivery device 200, similar to the drug delivery device 100 illustrated in FIG. 1. Dose setting mechanism 216 comprises a drug delivery device housing 220 and a dose dial component 222 that is positioned internally within the housing 220.

The dose dial component 222 is rotatable during a dosing step. In one example, the dose dial component 222 comprises a number sleeve that has an helical groove 234 configured on an outer surface 225. Certain indicia may be provided along this outer surface 225, such as numerals, letters, logos, or color patterns such that the indicia may change as a user rotates the dose dial component 222 to set the dose.

The dose setting mechanism 216 of the drug delivery device 200 preferably further comprises a drive sleeve 224 and this sleeve 224 may be positioned in the dose dial component 222. A spindle (i.e., lead screw) 226, such as a rotating spindle, may be positioned within the drive sleeve 224.

The dose setting mechanism 216 further comprises a clutch 228, and as illustrated, this clutch may be positioned between the dose dial component 222 and the drive sleeve 224.

In general, the dose setting mechanism 216 operates to ensure that a user must dial a dose greater than a predetermined minimum dose before the selected dose can be administered. In order to ensure this occurs, a split threaded insert 201 is located within housing 220. When a dose less than the minimum dose is selected, the split threaded insert 201 is in an open state such that the thread or its parts is separated by a gap, i.e., in an open position. As such, when the dose dial component 222 is rotated to select a dose less than a minimum dose, the split threaded insert 201 creates a high friction state or condition between the female threads of the dose dial sleeve and male thread of the split threaded insert 201, which prevents the dose dial component from rotating back into the dose setting mechanism 216 during the attempt of a dose administration step, thereby preventing a dose from being administered.

One aspect of the presently proposed drug delivery device is characterized in that at least a predetermined minimum dose must be set using the dose dial sleeve in order to change the state of the split threaded insert 201 to the closed configuration, whereby dose delivery becomes possible due to a then reduced friction between the female threads of the dose dial sleeve and male thread of the split threaded insert 201. In other words, this split threaded insert 201 changes state (i.e., a high friction state or a low friction state) dependent upon the dose that is dialed. The presently disclosed drug delivery devices, such as drug delivery device 200, are applicable to any dose setting/drive mechanisms used to dispense the drug compound(s) or medicament which have components rotating during dose setting and dose dispensing, especially devices working similar to the devices described in WO 2004/078239 A1.

For example, FIG. 2 illustrates one possible location of a split threaded insert 201 in the dose setting mechanism 216 of the injection device 200. As can be seen in FIG. 2, the split threaded insert 201 resides between the dose dial component or dose dial sleeve 222 and the housing 220. The outer groove or thread 234 provided along an outer surface of the dose dial component 222 is in threaded engagement with a male member 208 of the split threaded insert 201. As will be explained in greater detail below, the male member 208 of the threaded insert 201 comprises a proximal (upper in FIG. 4) threaded portion 202 and a distal (lower in FIG. 4) threaded portion 204. This lower threaded component 204 has been fixed into the body housing 220. The dose dial component 222 rotates in one direction relative to the housing 220 during a dose setting step or dose setting procedure. The dial component 222 also rotates in an opposite direction relative to the housing 220 during a dose dispensing step or dose dispensing procedure.

Figure 3:
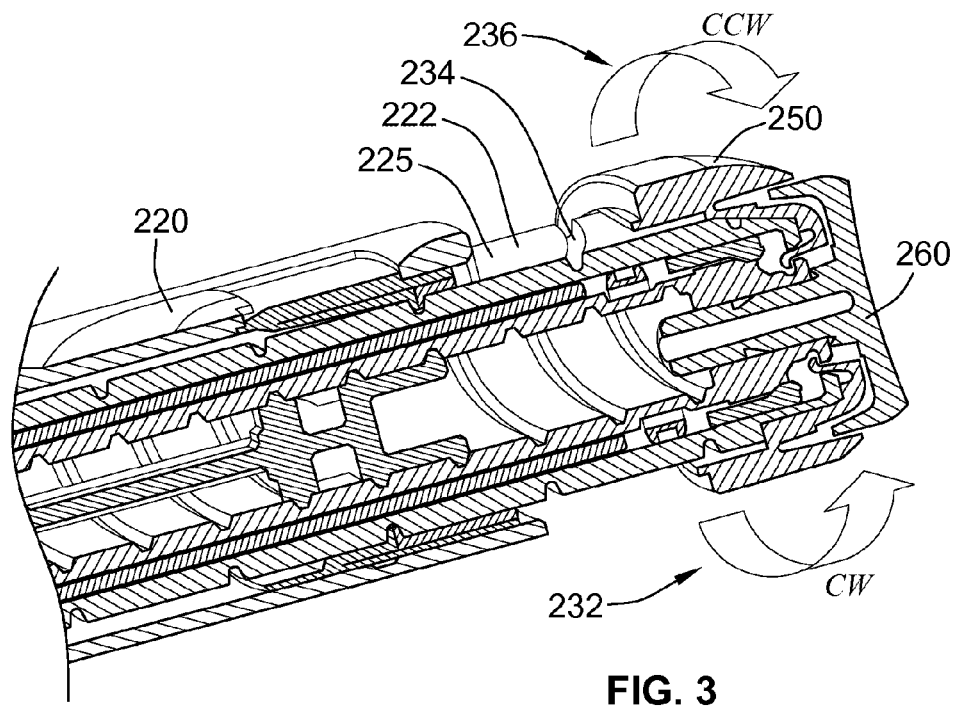
FIG. 3 illustrates a perspective cross-sectional view of a portion of the dose setting mechanism illustrated in FIG. 2 during an operation step.

FIG. 3 illustrates a perspective cross-sectional view of a portion of the dose setting mechanism illustrated in FIG. 2 during an operation step. In one preferred arrangement, the direction of rotation of the dosage selector 250 and the dose dial component 222 is clockwise (CW) 232 during a dose setting step and counter-clockwise (CCW) 236 during dispensing. During the dose setting step or procedure, the user applies a torque directly to the dosage selector 250. However, during a dose dispensing step or procedure, a dose button 260 is pressed in a distal direction (illustrated by arrow 214 in FIG. 2). Pressing on the dose button 260 causes the dose dial component 222 to backwind under the action of the applied axial button force provided that the dose set was equal to or greater than a predetermined minimum. In one preferred arrangement, pressing on the dose button 260 causes the dose dial component 222 to rotate in the counter clock wise direction as indicated by arrow 236.

Figure 4:
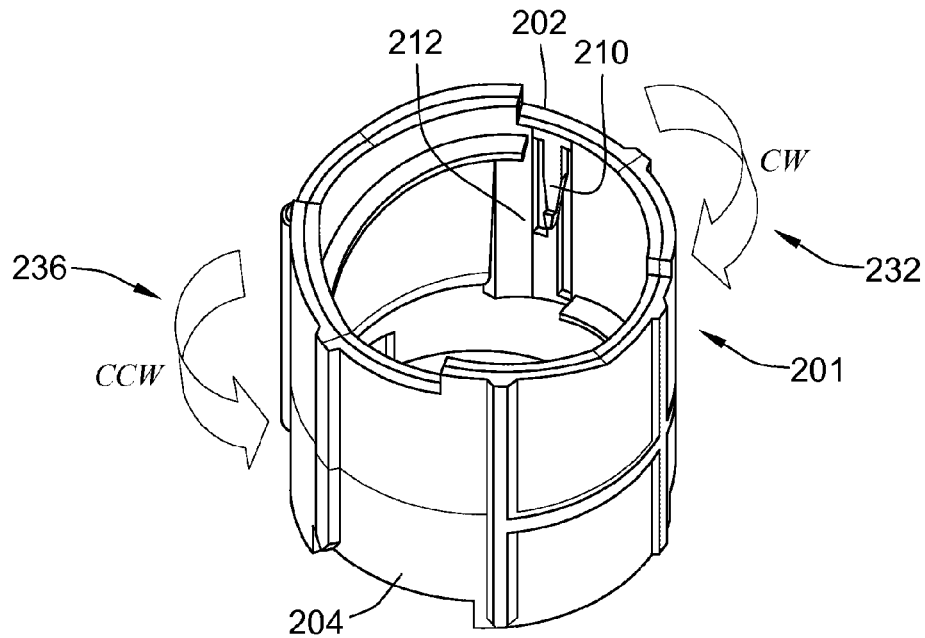
FIG. 4 illustrates a close-up perspective view of a split threaded insert that may be used with a dose setting mechanism, such as the dose setting mechanism illustrated in FIGS. 1-3.

FIG. 4 illustrates a perspective view of a split threaded insert 201 illustrated in FIG. 2. FIG. 5 illustrates a close-up sectional view of the split threaded insert 201 illustrated in FIG. 4 and FIG. 6 illustrates yet another close-up sectional view of the split threaded insert illustrated in FIG. 4. As may be seen from FIGS. 4-6, the split threaded insert 201 comprises an upper threaded portion 202 and a lower threaded portion 204. In one preferred arrangement, the split threaded insert 201 has been constructed such that the split line 227 between these first and second threaded portions 202, 204 forms a male helical thread portion 208. This may be seen from FIGS. 5 and 6. The first and second threaded portions 202, 204 are configured such that a relative rotation between these threaded portions 202, 204 serve to either widen/open up or narrow/reduce the gap between the upper and lower components 202 and 204. The lower threaded portion 204 is fixed to the body housing 220, whereas the upper threaded portion 202 may rotate by a fixed amount. The widening or opening up of a gap between the upper and lower threaded portions means that the effective width of the male thread form 208 increases. As such, this effective width of the male thread form will tend to introduce an increased amount of friction between the dose dial component 202 and the split threaded insert 201 and will thereby prevent the dose dial component 222 from rotating during a dose administration step, thereby preventing the dose from being delivered.

To dispense a dose, the dose dial component 222 must be overhauled or backwound into the drug delivery device 200 in a distal direction. For example, in FIG. 3, a dose dispensing step is illustrated where the dose dial sleeve is rotated in the CCW direction indicated by arrow 236. The high friction state resulting from a wider thread form 208 between the upper 202 and lower 204 threaded components of the split thread insert 201 is sufficient to prevent backwinding of the dose dial component 222. This causes the dose dial component 222 to lock during an attempted dose delivery. By controlling the point at which the threaded male portion 208 changes from an open (a wider thread) to a closed (a narrower thread) condition, then the point at which the dispense function is enabled/disabled can be controlled. Maintaining the threaded male portion 208 in its open (high friction state) condition below a predetermined minimum dose limit will tend to help ensure that the drug delivery device 200 cannot be used to dispense doses lower than this limit because the dose dial component 222 will lock when attempting to dispense, but will allow the user to manually cancel the dose by dialling back down to the zero position.

FIG. 6 illustrates an alternative cross-sectional view of the split threaded insert 201. As may be seen from FIG. 6, the upper threaded component 202 further comprises a flexible finger 210 provided along an inner wall surface 203 of the upper threaded component. In addition, a stop 212 is provided on an inner wall surface 205 of the lower threaded component 204. The flexible finger 210 acts to bias the upper threaded portion 202 to be either in the open or closed position by pushing against the stop 212.

FIG. 7 illustrates a perspective view of an initial position of the split threaded insert illustrated in FIGS. 4-6 situated along the dose dial component before a dose is selected. As illustrated, the dose dial component 222 further comprises a plurality of pips positioned along the outer surface 225 of the dose dial component 222. FIG. 7 illustrates the dose dial component in an initial position. As illustrated in FIG. 7, the dose dial component comprises a first pip 230 and a second pip 240 provided along an outer surface 225 of the dial component 222. As will be discussed in greater detail below, the first and second pips 230, 240 serve to bias the flexible finger 210 of the threaded insert 201 to either side of the stop 212 depending on the direction of rotation of the dose dial component 222.

FIG. 7 illustrates the upper threaded component 202 in conjunction with the dose dial component 222 and pips 230 and 240. Initially, when the dose dial component is wound back into the dose setting mechanism 216, the first pip 230 acts to force or reset the flexible finger 210 to the right of the stop thus biasing the upper threaded sleeve 202 in a counter-clockwise direction which serves to open up the threads. As previously mentioned, opening up these threads helps to induce a higher friction condition or locking configuration. In this initial state, the user may still wind the dose dial component 222 proximally out of the dose setting mechanism 216 because the torque applied to the dose dial component via the dosage selector is sufficient to overcome this friction in the dial direction (i.e., in the clockwise direction as illustrated by the arrow 232 in FIG. 3).

During a dose setting step of the device, the dose dial component 222 is wound out of the dose setting mechanism in a clockwise proximal direction (CW). In a preferred arrangement, the dose dial component 222 is wound out of the dose setting mechanism in a clockwise proximal direction (CW) as the dose setting mechanism follows a helical path defined by the threaded interface between the split threaded insert 201 and the dial component 222.

On dose dispense, the dial component 222 is overhauled by an axial load applied at the button 260 (illustrated in FIGS. 2 and 3) and this causes the dose dial component 222 to rotate in the counter-clockwise (CCW) direction (axially) back into the dose setting mechanism 216 as the drug contained within the drug delivery device is dispensed. Since high friction at the dose dial component-split thread insert 201 engagement will prevent this overhaul and thus the dispense function, rotating the upper threaded insert 202 in the counter-clockwise (CCW) direction (i.e., opening the thread) will induce high friction and therefore disable the dispense functionality. Rotating the threaded insert 201 clockwise (CW) will reduce the friction resulting in a low friction state therefore enabling full dispensing functionality. In this way control of the thread gap within the split threaded insert 201 will control the dispense state.

The specific operation of the split threaded insert 201 in relation to the operation of the drug delivery device 200 and the setting of a dose that meets or exceeds an absolute minimum dose can be explained as follows with reference to FIGS. 7-13. For example, FIG. 7 illustrates the combination thread portion 208 in an open position. Such an open position may be present just prior to when the drug deliver device 200 is used to set a first dose or alternatively just after the administration of a dose of medicament. In addition, such an open position may be induced at a plurality of points in the dose setting operation via appropriate positioning of the pips 230 and 240. FIG. 8 illustrates a cut away view of the drug delivery device illustrated in FIG. 7 illustrating that the combination thread portion 208 resides in a first configuration: an open position residing in groove 234.

Figure 9:
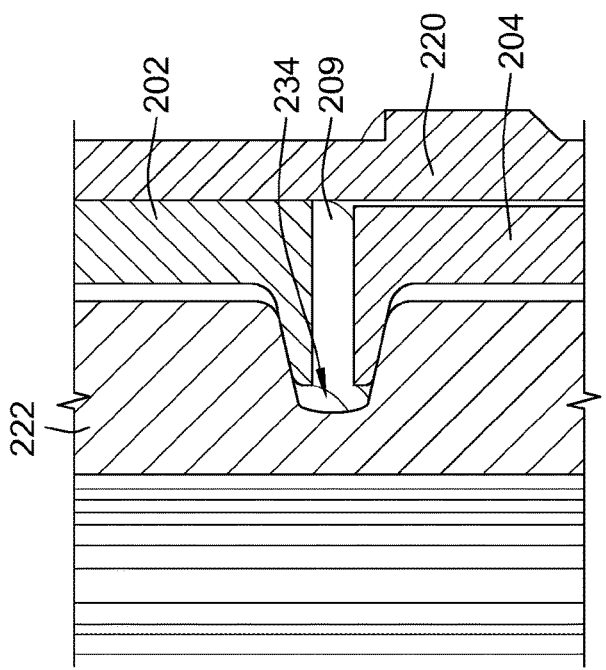
FIG. 9 illustrates a close up view of the split threaded insert illustrated in FIGS. 7-8.

Initially, the first pip 230 forces the flexible finger 210 of the upper threaded portion to the right as shown in FIG. 7. As a consequence, this also forces it to the right of the stop 212 on the lower threaded portion 204. As such, the upper threaded portion 202 is biased in a counter-clockwise (CCW) direction and this will tend to force the threads to the open position. In the open position, the system may be dialled out for setting a dose, but is locked for dispensing a dose unless a predetermined minimum dose or greater has been selected. FIG. 9 illustrates a close up view of the threaded portion 208 in this open configuration residing in groove 234. As can be seen from FIG. 9, a gap 209 resides between upper threaded portion 202 and the lower threaded portion 204.

During a dose setting step, the user directly winds out the dose dial component 222 via the dosage selector 250. This can overcome any additional thread friction between the thread form 208 and the outer groove 234 of the dose dial component. However, on dispensing a selected dose the system is sensitive to excess thread friction. As a consequence, if the selected dose is less than the minimum allowable dose, the system locks up during overhaul or back winding of the dose dial component back into the housing (i.e., during a dose dispensing step).

Figure 10:
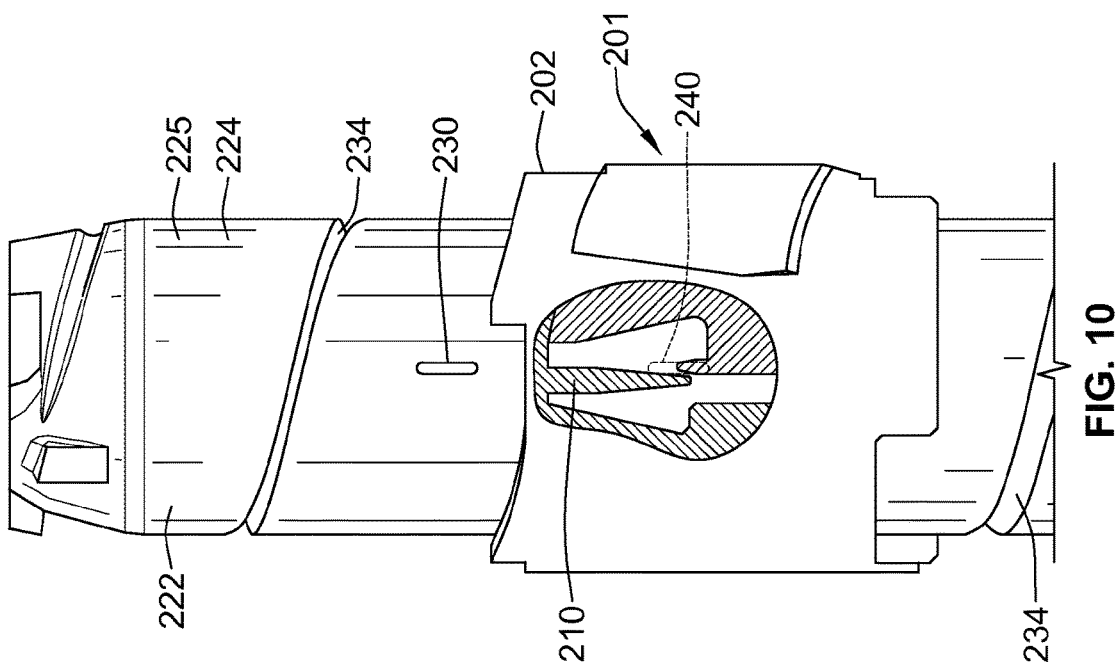
FIG. 10 illustrates a perspective view of a second position of the split threaded insert disposed along the dose dial component after a minimal dose has been selected.

FIG. 10 illustrates a situation where the drug delivery device has been used to select a minimum predetermined dose and the dose dial component has been dialled out from the drug delivery device. For example, in this situation, as the dose dial component 222 is rotated in the clockwise direction, the second pip 240 rotates along with the dial component. As the dose dial component continues to be rotated and once a certain minimum established dose has been met or exceeded (as could be visualized by way of the drug delivery device lens or window), the second pip 240 acts on the flexible finger 210.

FIG. 11 illustrates a cross sectional view of the second configuration of the split threaded insert disposed along the dose dial component after the minimal dose has been selected as illustrated in FIG. 10. FIG. 12 illustrates a close up view of the split threaded insert illustrated in FIGS. 10-11 and FIG. 13 illustrates an alternative close up view of the split threaded insert illustrated in FIGS. 10-12.

Figure 13:
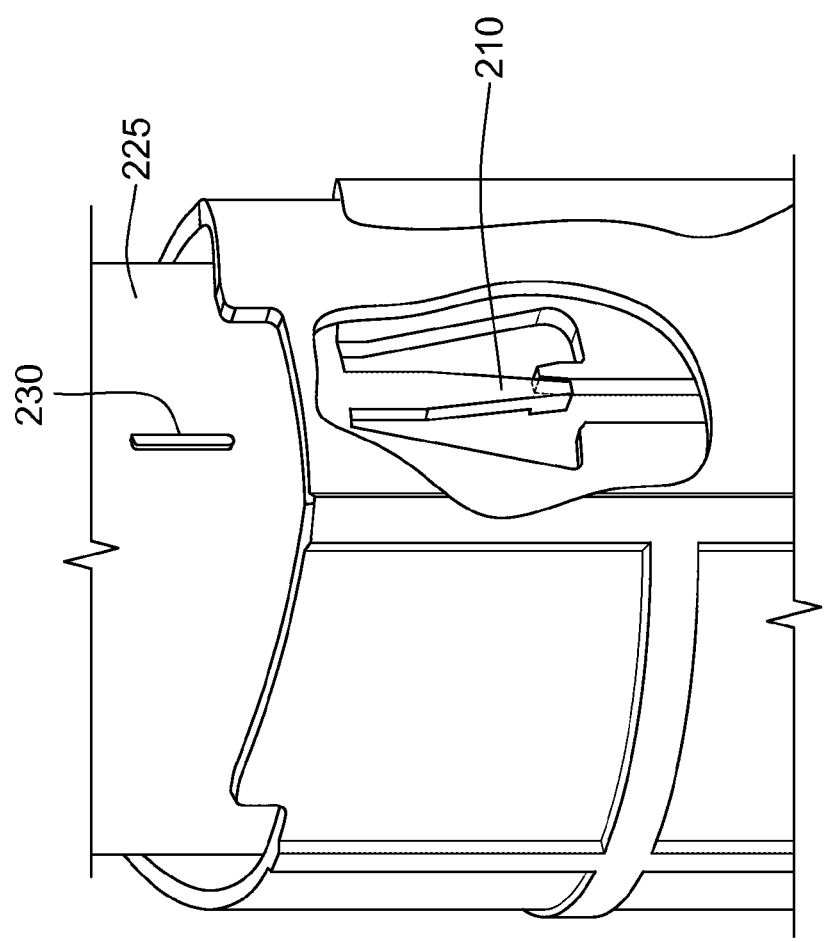
FIG. 13 illustrates an alternative close up view of the split threaded insert illustrated in FIGS. 10-12.

As can be seen from FIGS. 11-13, when acting on the flexible finger 210, the second pip 240 forces the finger 210 to rotate to the left, causing the upper threaded potion 202 to rotate in a clockwise (CW) direction. As such, the upper threaded portion 202 will tend to be biased the clockwise (CW) direction. This forces the threads to a closed position. For example, as can be seen from FIG. 12, this close up view of the split threaded insert illustrates that there is no longer a gap between the upper threaded portion 202 and the lower threaded portion 204 in this closed or second configuration. In this closed configuration, the two portions provide for the dose dial component 222 to now be essentially free running (i.e., reduced thread friction) within groove 234. This means that the drug delivery device 200 has now been enabled to dispense a dose greater than a certain predefined minimum dose and that the dose dial component 222 is capable of being overhauled/backwound in a distal direction into the housing 220 of dose setting mechanism 216 during dose administration. Higher doses may be set and dispensed if required, by manually winding the dose dial component out of the dose setting mechanism by way of the dosage selector 250.

At the end of a dispensing stroke when the dose dial component has been returned to its initial position as illustrated in FIGS. 7-9, the first pip 230 returns or resets the flexible finger 210 to the right back to the starting position. This action resets the split thread insert 201 to an initial open or widened configuration as previously described herein. The second pip 240 does not push the flexible finger 210 to the right during dispensing as it is chamfered in the return direction (i.e., dispensing).

One advantage of the presently disclosed drug delivery device design is that the basic operation of the drug delivery device remains unchanged with the exception of the lock out functionality occurring if a minimum dose is not dialled. In addition to this, the direct force feedback to the user that the device is locked up and a minimum dose has not been dialled is of significant benefit. In addition further visual feedback of the device's status, either 'locked' or 'ready to dispense', could be given to the user by providing a window (not shown) in the body housing 220 through which the relative position of the upper threaded component 202 can be observed. For example, a green portion of the upper threaded component 202 may only be visible through the window in the 'closed' position whereas in the 'open' position a red portion is visible.

In a preferred embodiment a master drug compound, such as insulin, contained within a multiple dose, user selectable device could be used with a single use, user replaceable, module that contains a single dose of a secondary medicament and the single dispense interface. When connected to the primary device, the secondary compound is activated/delivered on dispense of the primary compound. Although the present application specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our invention.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

As disclosed herein, the term "insulin" shall mean Insulin, insulin analogs, insulin derivatives or mixtures thereof, including human insulin or a human insulin analogs or derivatives. Insulin analogues are for example Gly(A21), Arg(B31), Arg(B32) human insulin; Lys(B3), Glu(B29) human insulin; Lys(B28), Pro(B29) human insulin; Asp (B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates. Exemplary embodiments of the present drug delivery device have been described. Those skilled in the art will understand, however, that changes and modifications may be made to these embodiments without departing from the true scope and spirit of the presently proposed drug delivery device, which is defined by the claims.

The invention claimed is:

1. Dose setting mechanism for a drug delivery device, the mechanism comprising:
a drug delivery device housing;
a dose dial component positioned at least partly in the housing and rotatable during dose setting and dose delivery; and
a split threaded insert in threaded engagement with a helical groove of the dose dial component, wherein the split threaded insert comprises a thread, a first portion, and a second portion,
wherein the split threaded insert is configured such that when the dose dial component is rotated, the first portion and the second portion move relative to each other such that the split threaded insert transforms from
a first configuration in which the thread or parts of the thread are in an open state to
a second configuration in which the thread or parts of the thread are in a closed state.

2. Mechanism according to claim 1 wherein in the first configuration of the split threaded insert, friction between the split threaded insert and the dose dial component when moved relative to each other is higher compared to the second configuration of the split threaded insert.

3. Mechanism according to claim 1 wherein the first portion is a proximal threaded portion and the second portion is a distal threaded portion.

4. Mechanism according to claim 3 wherein the distal threaded portion of the split threaded insert is fixed axially and rotationally to the drug delivery device housing.

5. Mechanism according to claim 3 wherein the proximal threaded portion of the split threaded insert comprises a flexible finger that engages a stop on the distal threaded portion of the split threaded insert.

6. Mechanism according to claim 1 wherein the dose dial component comprises at least one pip.

7. Mechanism according to claim 5
wherein the flexible finger engages a first pip of the dose dial component causing the split threaded insert to transform into the first configuration and/or
wherein the flexible finger engages a second pip of the dose dial component causing the split threaded insert to transform into the second configuration.

8. Mechanism according to claim 3 wherein the proximal and distal threaded portions mate to form a thread.

9. Mechanism according to claim 8 wherein the thread is a male thread and wherein the male thread comprises an enlarged male thread when the dose dial component has been rotated to a set dose that is less than a predetermined minimum set dose and/or comprises a reduced male thread when the dose dial component has been rotated to set a dose equal to or greater than a predetermined minimum.

10. Mechanism according to claim 1 wherein a set dose cannot be delivered when the thread is in the first configuration.

11. Mechanism according to claim 5 wherein the dose dial component comprises a first pip and a second pip, wherein a distance between the first pip and the second pip is proportional to a predetermined minimum set dose.

12. Mechanism according to claim 1 wherein a male threaded portion of the split threaded insert is in threaded engagement with a groove provided on an outer surface of the dose dial component.

13. Mechanism according to claim 1 wherein the dose setting mechanism further comprises a visual indication that notifies a user that a dose less than a predefined minimum dose has been dialed.

14. Dose setting mechanism for a drug delivery device, the mechanism comprising:
a drug delivery device housing;
a dose dial component positioned at least partly in the housing and rotatable during dose setting and dose delivery; and
a split threaded insert in threaded engagement with a helical groove of the dose dial component, wherein the split threaded insert comprises a thread, a first portion, and a second portion, wherein the split threaded insert is configured such that when the dose dial component is rotated, the first portion and the second portion rotate relative to each other such that the split threaded insert transforms from a first configuration in which the thread or parts of the thread are in an open state to a second configuration in which the thread or parts of the thread are in a closed state.

15. Dose setting mechanism for a drug delivery device, the mechanism comprising:
    a drug delivery device housing;
    a dose dial component positioned at least partly in the housing and rotatable during dose setting and dose delivery; and
    a split threaded insert in threaded engagement with a helical groove of the dose dial component, wherein the split threaded insert comprises a thread,
    wherein the split threaded insert is configured such that when the dose dial component is rotated, the split threaded insert transforms from
    a first configuration in which the thread or parts of the thread are in an open state to
    a second configuration in which the thread or parts of the thread are in a closed state,
    wherein the split threaded insert comprises a proximal threaded portion and a distal threaded portion,
    wherein the proximal and distal threaded portions mate to form a thread, and wherein the thread is a male thread and wherein the male thread comprises an enlarged male thread when the dose dial component has been rotated to a set dose that is less than a predetermined minimum set dose and/or comprises a reduced male thread when the dose dial component has been rotated to set a dose equal to or greater than a predetermined minimum.

16. Dose setting mechanism for a drug delivery device, the mechanism comprising:
    a drug delivery device housing;
    a dose dial component positioned at least partly in the housing and rotatable during dose setting and dose delivery; and
    a split threaded insert in threaded engagement with a helical groove of the dose dial component, wherein the split threaded insert comprises a thread,
    wherein the split threaded insert is configured such that when the dose dial component is rotated, the split threaded insert transforms from
    a first configuration in which the thread or parts of the thread are in an open state to
    a second configuration in which the thread or parts of the thread are in a closed state, and
    wherein a male threaded portion of the split threaded insert is in threaded engagement with a groove provided on an outer surface of the dose dial component.

* * * * *